(12) United States Patent
Nempont et al.

(10) Patent No.: US 11,123,036 B2
(45) Date of Patent: Sep. 21, 2021

(54) IMAGE REGISTRATION

(71) Applicant: KONINKLIJKE PHILIPS N.V., Eindhoven (NL)

(72) Inventors: Olivier Pierre Nempont, Suresnes (NL); Thijs Elenbaas, Nijmegen (NL); Javier Olivan Bescos, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 869 days.

(21) Appl. No.: 15/736,000

(22) PCT Filed: Jun. 3, 2016

(86) PCT No.: PCT/EP2016/062576
§ 371 (c)(1),
(2) Date: Dec. 13, 2017

(87) PCT Pub. No.: WO2016/206942
PCT Pub. Date: Dec. 29, 2016

(65) Prior Publication Data
US 2018/0168532 A1    Jun. 21, 2018

(30) Foreign Application Priority Data

Jun. 25, 2015   (EP) .................................... 15305992

(51) Int. Cl.
*A61B 6/00*       (2006.01)
*A61B 6/12*       (2006.01)
(Continued)

(52) U.S. Cl.
CPC .............. *A61B 6/5235* (2013.01); *A61B 6/12* (2013.01); *A61B 6/463* (2013.01); *A61B 6/469* (2013.01);
(Continued)

(58) Field of Classification Search
CPC ..... A61B 6/5235; A61B 6/5211; A61B 6/463; A61B 6/469; A61B 6/12; A61B 6/487;
(Continued)

(56) References Cited

U.S. PATENT DOCUMENTS

2005/0182319 A1*  8/2005  Glossop ................... A61B 5/20
                                                              600/424
2008/0140087 A1*  6/2008  Barbagli .................. B25J 13/02
                                                              606/130
(Continued)

FOREIGN PATENT DOCUMENTS

WO        2011121504 A1    10/2011
WO        2012011035 A1     1/2012
(Continued)

OTHER PUBLICATIONS

Truong, Michael et al "Analysis of Catheter-Based Registration with Vessel-Radius Weighting of 3D CT Data to 2D X-ray for Cardiac Catheterisation Procedures in a Phantom Study", Statistical Atlases and Computational Models of the Heart, Imaging and Modelling Challenges, 2011, pp. 139-148.
(Continued)

*Primary Examiner* — Bo Joseph Peng

(57) ABSTRACT

In cardiac roadmapping, a "roadmap", which is typically a representation of the vasculature of a patient obtained via previously acquired data from a CT scan, is overlaid on live intervention data, showing the position of an intervention device obtained using fluoroscopy. In this way, the intervention device may be tracked inside a realistic representation of the patient. The accurate registration of the fluoroscopic image to the roadmap data is an important step, otherwise the reported live position of the intervention device would not be shown at an accurate position inside the roadmap. Registration can be performed by the injection of contrast medium. In the case of cardiac roadmapping, the
(Continued)

small vessel diameters mean that it is possible to register intervention devices directly. However, the behavior of intervention devices in larger vessels is difficult to predict, and so device-based registration is harder to achieve in such a context. By detecting the presence of a specific intervention device and a specific vascular context, an accurate registration of the intervention device to the 3D roadmap can be provided via comparison to a library of known device configurations.

19 Claims, 6 Drawing Sheets

(51) Int. Cl.
  *G06T 7/33* (2017.01)
  *G06T 7/30* (2017.01)
  *G16H 50/70* (2018.01)
  *A61B 90/00* (2016.01)

(52) U.S. Cl.
  CPC ............ *A61B 6/487* (2013.01); *A61B 6/5211* (2013.01); *G06T 7/30* (2017.01); *G06T 7/344* (2017.01); *A61B 2090/365* (2016.02); *G06T 2207/10081* (2013.01); *G06T 2207/10121* (2013.01); *G06T 2207/20012* (2013.01); *G06T 2207/30021* (2013.01); *G06T 2207/30101* (2013.01); *G16H 50/70* (2018.01)

(58) Field of Classification Search
  CPC ..... A61B 2090/365; G06T 7/344; G06T 7/30; G06T 2207/20012; G06T 2207/10081; G06T 2207/10121; G06T 2207/30021; G06T 2207/30101; G16H 50/70; G16H 50/20

See application file for complete search history.

(56) References Cited

U.S. PATENT DOCUMENTS

| | | | |
|---|---|---|---|
| 2008/0192895 A1* | 8/2008 | Dehler | A61B 6/4405 378/94 |
| 2009/0137952 A1* | 5/2009 | Ramamurthy | A61B 5/4887 604/95.01 |
| 2011/0038517 A1* | 2/2011 | Mistretta | A61B 6/5247 382/128 |
| 2012/0022544 A1* | 1/2012 | Chang | A61B 6/5211 606/97 |
| 2013/0215249 A1* | 8/2013 | Papalazarou | H04N 7/18 348/77 |
| 2013/0336558 A1 | 12/2013 | Manzke | |
| 2014/0228678 A1 | 8/2014 | Meyer | |
| 2014/0294152 A1 | 10/2014 | Florent | |
| 2014/0371578 A1 | 12/2014 | Auvray | |

FOREIGN PATENT DOCUMENTS

| | | |
|---|---|---|
| WO | 2014020495 A1 | 2/2014 |
| WO | 2014207188 A1 | 12/2014 |

OTHER PUBLICATIONS

Ambrosini, Pierre et al "Continuous Roadmapping in Liver Tace Procedures using 2D-3D Catheter-based Registration", International Journal of Computer Assisted Radiology and Surgery, vol. 10, No. 9, May 2015, pp. 1357-1370.

* cited by examiner

2a)

2d)

2b)

2e)

2c)

2f)

IMAGE REGISTRATION

CROSS-REFERENCE TO PRIOR APPLICATIONS

This application is the U.S. National Phase application under 35 U.S.C. § 371 of International Application No. PCT/EP2016/062576, filed on Jun. 3 2016, which claims the benefit of European Patent Application No. 15305992.8, filed on Jun. 25, 2015. These applications are hereby incorporated by reference herein.

FIELD OF THE INVENTION

The present invention relates to an apparatus for intervention object based registration during adaptive image road mapping of an object of interest, an X-ray imaging system, a method for intervention object based registration during adaptive image road mapping of an object of interest, a computer program element, and a computer-readable medium.

BACKGROUND OF THE INVENTION

During an endovascular intervention, a medical professional may use three-dimensional CT data to provide a convenient "road map" of a vascular network. Through the provision of a 2D fluoroscopic image (live data), and its fusion with the 3D CT data, a roadmap can be displayed on the live data, showing the position of an intervention device in the object of interest. The 3D data is projected onto an image plane of the live data at the same angle as that of the X-ray used in the 2D fluoroscopic acquisition. There remains the problem of registering the 2D fluoroscopic image to the 3D data.

To perform this registration, one approach is to make an injection of contrast agent into a patient's vasculature. This enables the full extent of the vessels to be discerned in the fluoroscopic data. Then, comparison of the vessels with the vessels in the 3D CT data enables the registration of vessels in the three-dimensional data with vessels in the live fluoroscopic images.

Another technique enables registration without the injection of contrast medium. This registration technique uses bony structures, such as a spinal section, which will be common across the CT and fluoroscopy data. An injection of contrast agent is not needed. This, however, can result in lower registration accuracy, because the registration is not performed directly using the target vasculature, but rather proximal bony structures.

Interventional devices that are inserted into the vessels may be used to perform registration on vessels without the injection of contrast medium. However, conventionally, this technique can only be used when the devices are inserted into small vessels, because then the shapes of the interventional device and of the vessel are similar. In other situations, such a technique is not as successful when the interventional device is introduced into a large space, such as a vessel with a much greater cross section than that of an inserted device, such as a large aneurysm.

WO 2012/011035 discusses an adaptive road mapping technique.

US2014/294152 discusses an apparatus for pairing an anatomy representation with live images.

SUMMARY OF THE INVENTION

It would be advantageous to have an improved technique for providing intervention device based registration during adaptive image road mapping of an object of interest.

Towards this end, a first aspect of the invention provides an apparatus for intervention device based registration during adaptive image road mapping of an object of interest.

The apparatus comprises an input unit, and a processing unit.

The input unit is configured to provide object data of a region of interest of an object, to provide intervention image data of the region of interest, wherein the image comprises intervention device information of an intervention device positioned in the region of interest, and a configuration reference map, wherein the configuration reference map comprises: (i) reference object information and (ii) reference intervention device information of a reference intervention device inside the reference object information.

The processing unit is configured to perform a first registration to match the intervention device information to the reference intervention device information in the configuration reference map, to yield a matched configuration reference map registration. The processing unit is configured to perform a second registration to match the object data with the reference object information of the matched configuration reference map to yield an object data registration, and to combine the matched configuration reference map registration and the object data registration to yield final roadmap image data.

According to this aspect of the invention, intervention device information of an intervention device can be used to identify reference object information from a configuration reference map. The reference intervention device information is linked to the reference object information. Therefore, a library of configurations of intervention devices based on the type of intervention device, and of the arrangement of the reference object, may be used to provide a more accurate registration of the intervention device in the object data of the region of interest.

In other words, by detecting the type of intervention device used, a library of intervention devices in different anatomical contexts is consulted. A configuration reference map match corresponding to the intervention device in the intervention image can be obtained. This enables the reference object information to be used to provide final roadmap image data with improved registration accuracy.

According to a second aspect of the invention, an X-ray imaging system is provided.

The X-ray imaging system comprises: an X-ray acquisition device with an X-ray source and an X-ray detector for capturing live X-ray images. The X-ray imaging system further comprises an apparatus for intervention device based registration for adaptive image road mapping of an object of interest as previously described, and a display device.

The X-ray imaging system is configured to acquire live X-ray image data of a region of interest of an object, to provide the live X-ray image data to the input device of the device for adaptive image road mapping, and to display the live X-ray images with an adaptive image roadmap on the display device.

According to a third aspect of the invention, a method is provided for intervention device based registration during adaptive image road mapping of an object of interest. The method comprises the steps of:

a) providing object data of a region of interest of an object;
b) providing intervention image data of the region of interest, wherein the image data comprises intervention device information of an intervention device positioned in the region of interest;
c) providing a configuration reference map, wherein the configuration reference map comprises (i) reference object information and (ii) reference intervention device information of a reference intervention device inside the reference object information;

d) performing a first registration to match the intervention device information to the reference intervention device information in the configuration reference map, to yield a matched configuration reference map registration;

e) performing a second registration to match the object data with the reference object information of the matched configuration reference map to yield the object data registration; and f) combining the matched configuration reference map registration and the object data registration to yield final roadmap image data.

According to a fourth aspect of the invention, there is provided a computer program element for controlling an apparatus according to the previous description which, when the computer program element is executed by a processing unit, is adapted to perform he method steps described previously.

According to a fifth aspect of the invention, a computer-readable medium is provided having stored the program element of the previous description.

In the following description, the term "object data" means data obtained by X-ray (or MRI, or other medical imaging modalities) which provides information about the anatomy of a patient. Typically, this information is 3D volumetric data containing a 3D representation of a vascular network of a patient. However, it will be appreciated that such object data containing vascular information could be two-dimensional object data of a patient. 3D object data would conventionally be obtained by a CT scan, or a C-arm scan. 2D object data could be obtained by a pre-operative X-ray, or angiograms acquired previously during the same intervention.

In the following description, the term "intervention image data" refers to live data obtained, for example, during an endovascular procedure monitored by a fluoroscope. A fluoroscope applies a succession of X-ray pulses through a region of interest of a patient. These are detected at the other side of the patient, thus giving information about the objects inside the region of interest. The information is a sequence of projective images of the region of interest where radiopaque elements are visible in the fluoroscope's field of view. Therefore, the intervention image data allows the tracking of the movement of an intervention device, such as a catheter, inside a patient. Any other objects visible in the patient using X-ray can also be observed, such as anatomical features comprising bony structures. In the case that contrast agent is injected, vessels containing contrast agent can be identified.

In the following description, the term "intervention device information" refers to a sector of the intervention image data which contains image information of an intervention device. Thus, the intervention device information may be a fluoroscopic representation of a stent or a catheter. In the following description, the term "configuration reference map" refers to a data record comprising reference object information of certain specific anatomical formations, and intervention device information of certain intervention devices.

In other words, the reference object information could comprise information about a common vessel configuration. A common vessel configuration could be considered to be an arcuate portion of a blood vessel, or a bifurcation of a vessel, or a curved vessel.

Reference intervention device information inside the reference object information could be considered to be a representation of catheters and stents. The stents may be an undeployed stent, or a partially deployed stent, or a fully deployed stent inside the reference object information. Therefore, the configuration reference map contains a common combination of anatomical features with intervention devices, wherein the intervention devices are optionally shown at various degrees of deployment.

Therefore, it can be seen as an approach of the invention to register object data with intervention image data using prior knowledge of possible anatomical configurations, and the shape of intervention devices in such commonly known anatomical configurations. A search can be made for a matching intervention device in the configuration reference map which enables the intervention device in the current live image to be registered to the reference intervention device. In the configuration reference map, the reference intervention device registration relationship to the reference object information is known. The reference object information in the configuration reference map can be registered to object data. By combining both registrations, final roadmap image data is obtained.

These and other aspects of the present invention will become apparent from, and be elucidated with reference to, the embodiments described hereinafter.

DETAILED DESCRIPTION OF EMBODIMENTS

There are several approaches to the registration of object data acquired pre-operatively, with intervention image data acquired live, for example via fluoroscopic means. An approach which uses contrast medium requires regular injections of contrast medium into the vasculature of a patient. The intervention image with contrast medium captures the extent of the contrast medium in a vasculature, which thus defines the vessel boundaries accurately.

The pre-operative object data (such as CT data) will show the boundaries of the vessel wall. Therefore, the sections of vasculature containing contrast agent in the intervention image data may be used to register the intervention image to the object data.

Then, the intervention image can be aligned with the object data, and a live position of an intervention image data in the object data can be shown in three dimensions. This process is known as registration.

Sometimes, it is desirable to capture the position of an intervention device in the vasculature without the injection of contrast medium, to reduce the amount of contrast medium injected into a patient during an intervention, or to be able to track an object that is moving due, for example, to breathing, or heart movement. When an intervention device is inserted into a small vessel, the shapes of the device and the vessel are similar. Therefore, the vasculature of the road map can be registered to the intervention devices in the fluoroscopic images to obtain an accurate registration without the injection of contrast medium.

Although such non-contrast registration techniques have been successful, problems arise when dealing with the position of an intervention device in large vascular structures (where the thickness of the intervention device is negligible, compared to the width of the vascular structure). In this case, the interventional device may float inside the vessel. Typically, it might not touch the vessel walls, and so a device-based registration is not possible.

Figure 1:
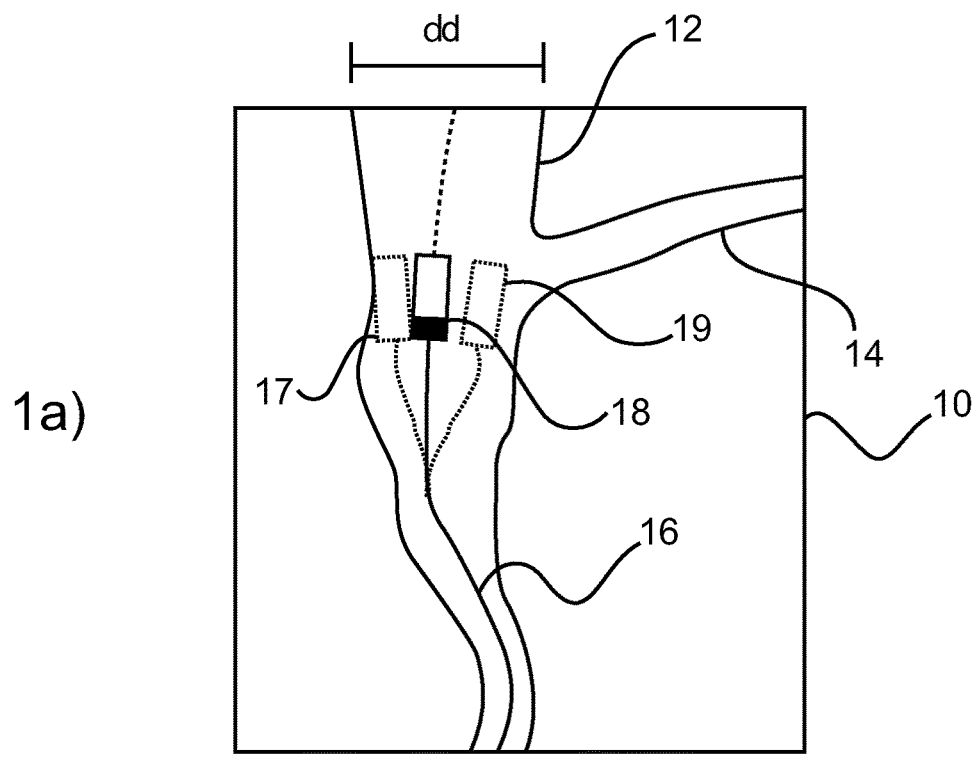
FIGS. 1a) and 1b) shows configurations of intervention devices in different vasculatures.
Figure 1:
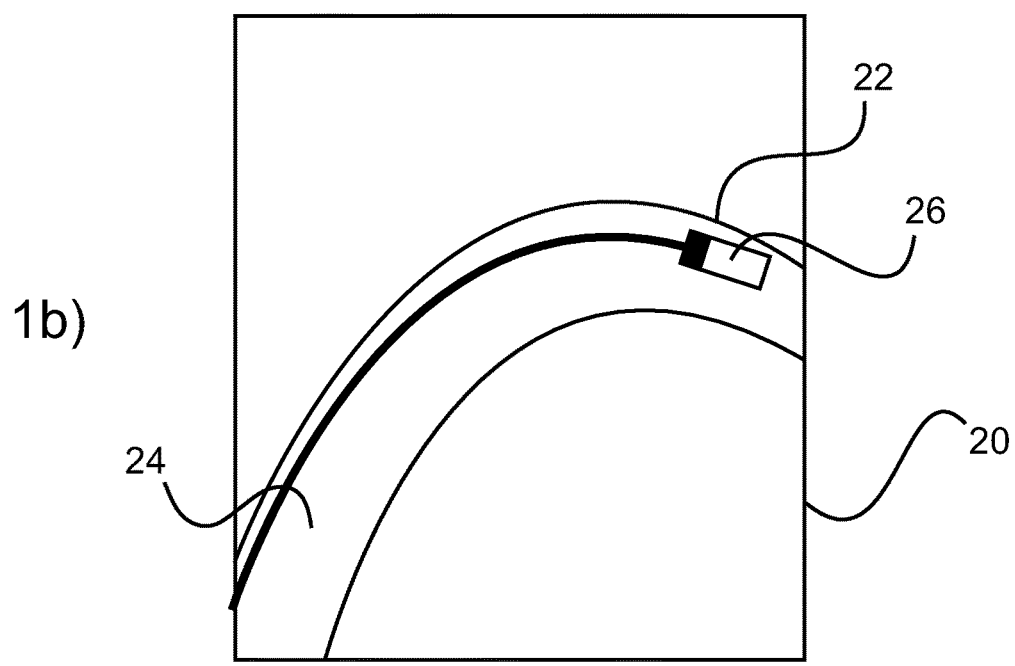

FIG. 1a) shows an intervention image frame taken from an example fluoroscopy frame 10. In this image is illustrated the part of a human vasculature 12 showing a large main body with a side branch 14. An intervention device 16 (a catheter) has been inserted into the large main body, for example, via a transfemoral approach. The large vessel 12 has a large thickness δd relative to the thickness of the intervention device 16. Therefore the intervention device 16 floats around inside the larger vessel in an unpredictable way, as shown with dotted lines at alternative positions 17 and 19. The ambiguity resulting from the difference in diameter of the intervention device 16 and the larger vessel enclosing it, makes device-based registration either impossible, or inaccurate.

FIG. 1b) shows a fluoroscopy frame 20 with a highly arcuate section of vasculature 22. An intervention device 24 (a catheter) has been inserted into the vasculature 22. In this case, it can be seen that the highly arcuate vessel prevents the intervention device 24 from moving around. Therefore, the ambiguity demonstrated in the case of a large vessel shown in FIG. 1a) can be solved, and the registration of the live intervention image with the 3D object data could still be performed.

Of course, it will be appreciated that there is a large variety of vessel configurations which allow determination of a registration in the manner discussed above, and the presence of a highly arcuate section is not essential, but merely presented as an example. Other situations leading to a predictable intervention device arrangement could be the cannulation of a side branch for example on the bifurcations, or the insertion of devices into both branches of a bifurcation, as shown at FIG. 2e) discussed below.

Figure 2:
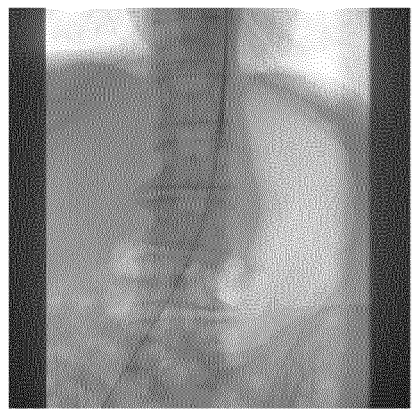
FIG. 2 shows various intervention scenarios.
Figure 2:
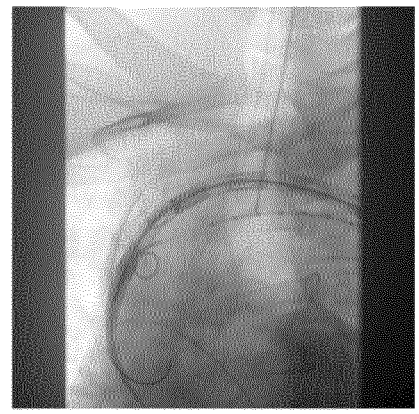
Figure 2:
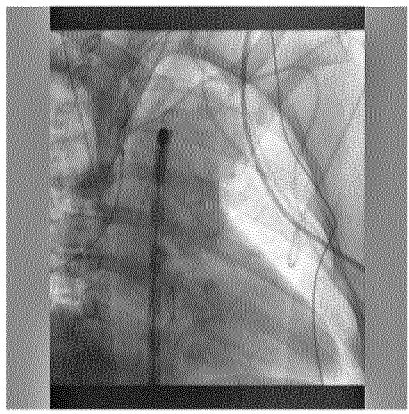
Figure 2:
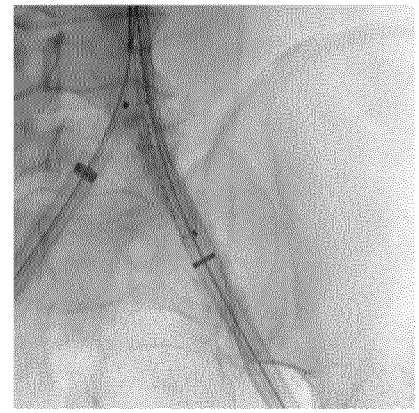
Figure 2:
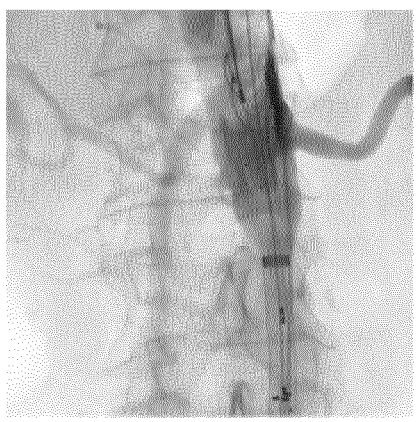
Figure 2:
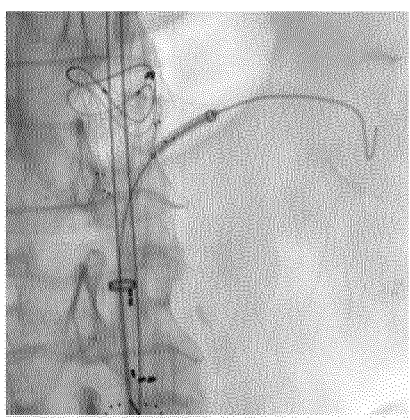

FIG. 2 shows practical examples of live intervention image data. In FIG. 2a), a catheter is seen in the abdominal aorta following the length of the spine. In FIG. 2b, an intervention device is shown approaching a heart. In FIG. 2c), an intervention device is shown inside a large aneurysm in the abdomen. In all of these cases, the position of the live intervention device will be ambiguous at a given moment, and so a device based registration applied to such images could result in a registration ambiguity.

In contrast, FIG. 2d) shows a situation in which an intervention device is positioned in a highly arcuate vessel. FIG. 2e) shows a situation in which two intervention devices are positioned diverging into both branches of an aortic bifurcation. FIG. 20 shows another situation where an intervention device is shown diverging into a side branch.

In the latter three cases, device-based registration is possible, because the anatomy and the individual characteristics of the intervention device imply a predictable registration between the live intervention image and the object data.

Figure 3:
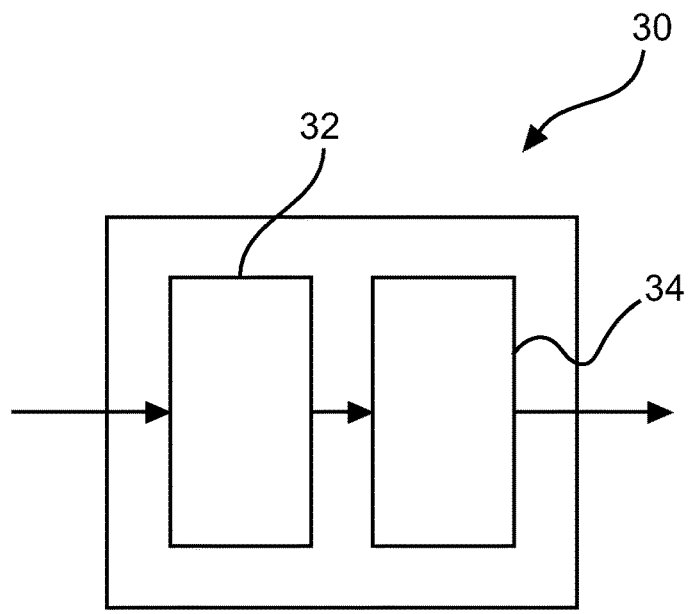
FIG. 3 shows an apparatus according to the first aspect.

FIG. 3 illustrates an apparatus according to a first aspect of the invention. There is provided an apparatus 30 for intervention device based registration during adaptive image road mapping of an object of interest, comprising an input unit 32 and a processing unit 34.

The input unit 32 is configured to provide object data of a region of interest of an object, to provide intervention image data of the region of interest, wherein the intervention image comprises intervention device information of an intervention device positioned in the region of interest, and a configuration reference map, wherein the configuration reference map comprises: (i) reference object information and (ii) reference intervention device information of a reference intervention device inside the reference object information.

The processing unit 34 is configured to perform a first registration to match the intervention device information to the reference intervention device information in the configuration reference map, to yield a matched configuration reference map registration; to perform a second registration to match the object data with reference object information of the matched configuration reference map to yield an object data registration; and to combine the matched configuration reference map registration and the object data registration to yield final roadmap image data.

Therefore, an apparatus according to this description enables intervention device based registration showing adaptive image road mapping, which exploits the particular characteristics of known intervention device inside candidate anatomical shapes, to improve the accuracy of a registration between object data of a region of interest of an object and intervention image data.

Figure 4:
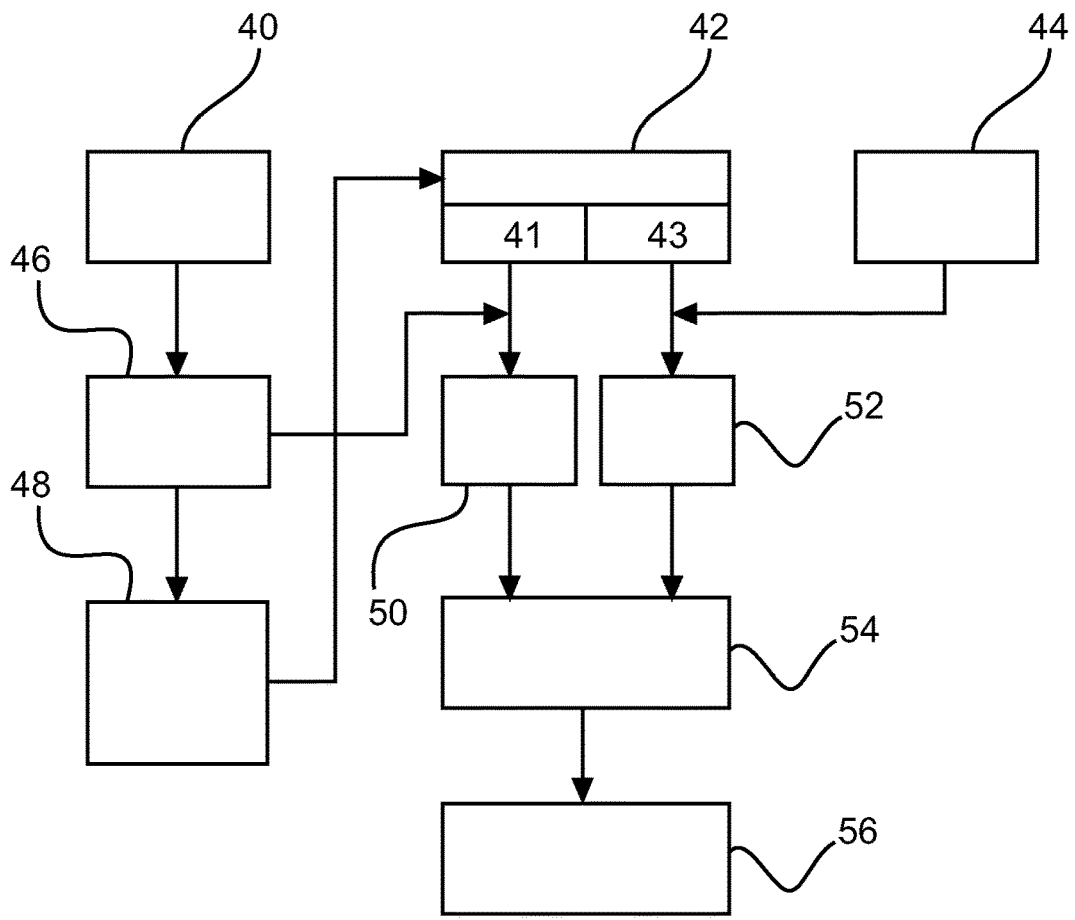
FIG. 4 shows an example of an implementation according to the first aspect.

FIG. 4 shows an exemplary implementation of an apparatus according to first aspect of the invention. In FIG. 4, a fluoroscopic image is provided as intervention image data 40. A configuration reference map database 42 is provided. In addition, object data 44 of a region of interest of an object is provided as a 3D road map of a vasculature.

The object data 44 of a region of interest of the object could be provided as a CT scan of a patient taken preoperatively. Alternatively, the object data 44 of a region of interest could be provided as a 2D X-ray image or another type of medical image, such as an MRI scan or a PET scan.

The intervention image data 40 is typically provided as a fluoroscopic image, although other methods providing "live" information about the position of a catheter in a region of interest of a patient during an intervention may be used.

The configuration reference map database 42 is provided as a database comprising records of different lumens, or sections of human vasculatures, with reference intervention device information of reference intervention devices positioned in those lumens.

Typically, such a database would be implemented on a computer storage system, such as a PC or a server connected to a network. The database could be held on a server accessed via the World Wide Web, or in a so-called "cloud" implementation. The database could be a subscription-based service. In an embodiment, subsets of configuration reference maps are stored in a local PC reflecting the clinical speciality of the operating lab. For example, the local PC may store only cardiac-based reference object information and reference intervention device information. In an embodiment, the PC may be updated via the World Wide Web to reconfigure the apparatus to function in a neurological intervention context.

The reference intervention device information 41 comprises exemplary intervention device deployments or configurations. It will be appreciated that the advantage is achieved even with only one configuration reference map, providing one reference object (of a common shape such as an arcuate vessel) and one common reference intervention device (such as a catheter). However, the configuration reference map database 42 may also be implemented as a plurality of configuration reference maps, which is searchable.

The reference object information 43 and the reference intervention device information 41 of the configuration reference map database 42 may be obtained from a corpus of multiple real-life patient examinations.

According to an embodiment of the invention, the reference intervention device information 41 can be taken from an examination of the real-life device in a patient.

Alternatively, the reference intervention device information 41 can be provided as a computer-generated model of a device generated using a mechanical solver.

In the implementation of FIG. 4, the fluoroscopic images are processed to detect intervention devices used during an endovascular procedure at box 46. Such devices are usually radiopaque, moving, and rectilinear. Therefore, these devices can be automatically detected in fluoroscopic images, for example. Then, at box 48, a detection of the current intervention device configuration with the reference intervention devices 41 of the configuration map is performed. The configuration reference map database 42 comprises reference object information 43 and reference intervention device information 41.

In a case where only one configuration reference map is present, this equates to a binary choice of the configuration reference map being suitable, or not.

In a case where a plurality of configuration reference maps is provided, the detected intervention device in the intervention image is compared to each record of reference intervention device information 41 in the configuration reference map to identify configuration reference maps suitable for registration.

Many image processing techniques, such as template matching algorithms, or machine learning approaches, can be used to achieve this task. When a reference device which matches the intervention device in the intervention image data 40 is identified, a first registration at box 50 is triggered. The detection of the intervention device configuration suitable for registration is shown in box 48.

Having detected an intervention device in the intervention image data 40, and found suitable matching reference intervention device information 41 in the configuration reference map database 42, one or more configuration maps are selected comprising reference object information 43 linked with the reference intervention device information 41. The first registration 50 of the detected intervention device is performed with the reference intervention device information 41 in the configuration reference map database 42. The detected intervention devices as detected in the fluoroscopic image and the reference intervention devices are registered. For this step, rigid registration methods, or deformation registration techniques could be used.

According to an embodiment of the invention, the selection of a configuration reference map may be performed by the matching of reference object information 43 of the configuration reference map database 42 to object data 44 of the region of interest.

Once the first registration 50 of the intervention device information to the reference intervention device information has been performed, the output of the first registration 50 is the resulting transform, the matched configuration map registration.

At box 52, a second registration is performed. The object data 44 is registered with the reference object information 43 of the matched configuration reference map. Therefore, in box 52, a registration of the object data (object data could be, for example, raw CT data, or a 3D mesh obtained from the segmentation of the raw CT data) with a 2D region or 3D mesh of the reference map indicated by the detected intervention image data is provided. The output is an object data registration.

Rigid registration methods, or deformable registration techniques can also be used. Deformations specific to the reference map are also possible. Once the first registration 50 and the second registration 52 have been performed, box 54 provides a combination of the first and second registration results. This enables registration of the 3D vasculature with the current fluoroscopic image, based on an intervention device in the intervention image data 40. The output of the process is a 3D road map which has been registered to the intervention image data 40 output by the fluoroscope at box 56.

Figure 5:
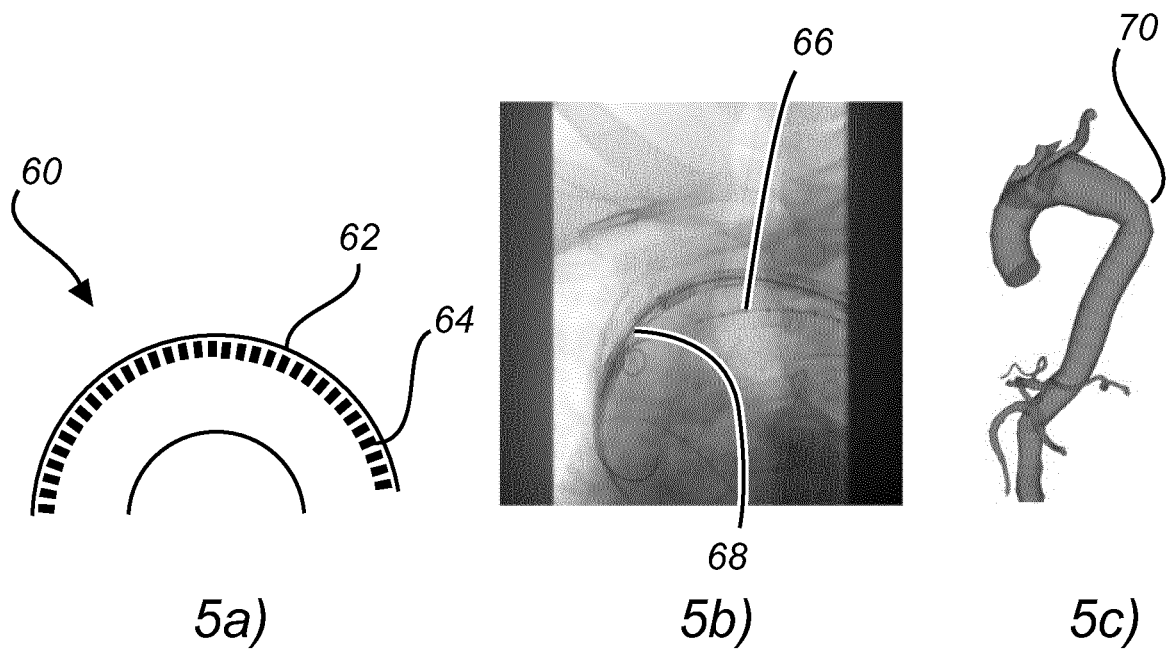
FIG. 5 shows a sequence illustrating the registration process.
Figure 5:
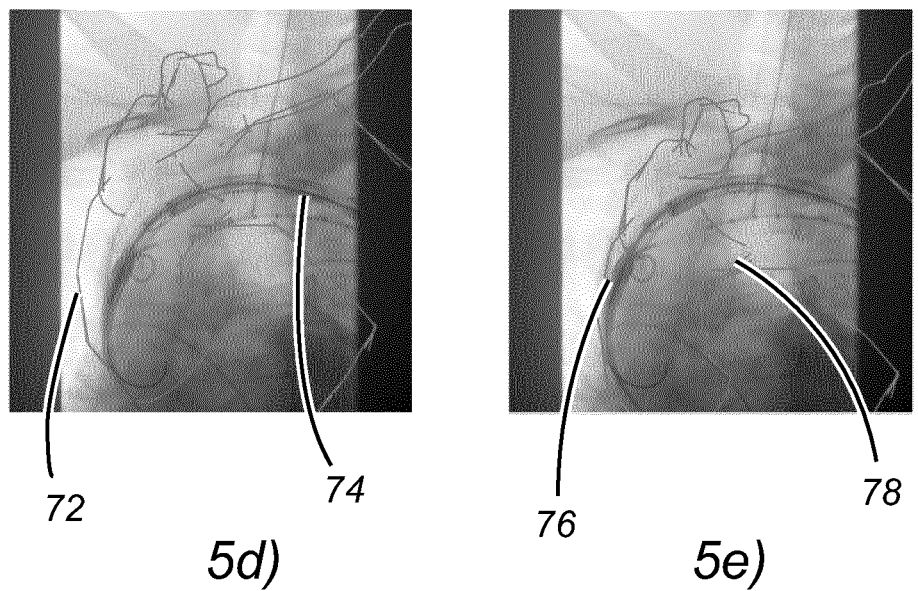
Figure 6:
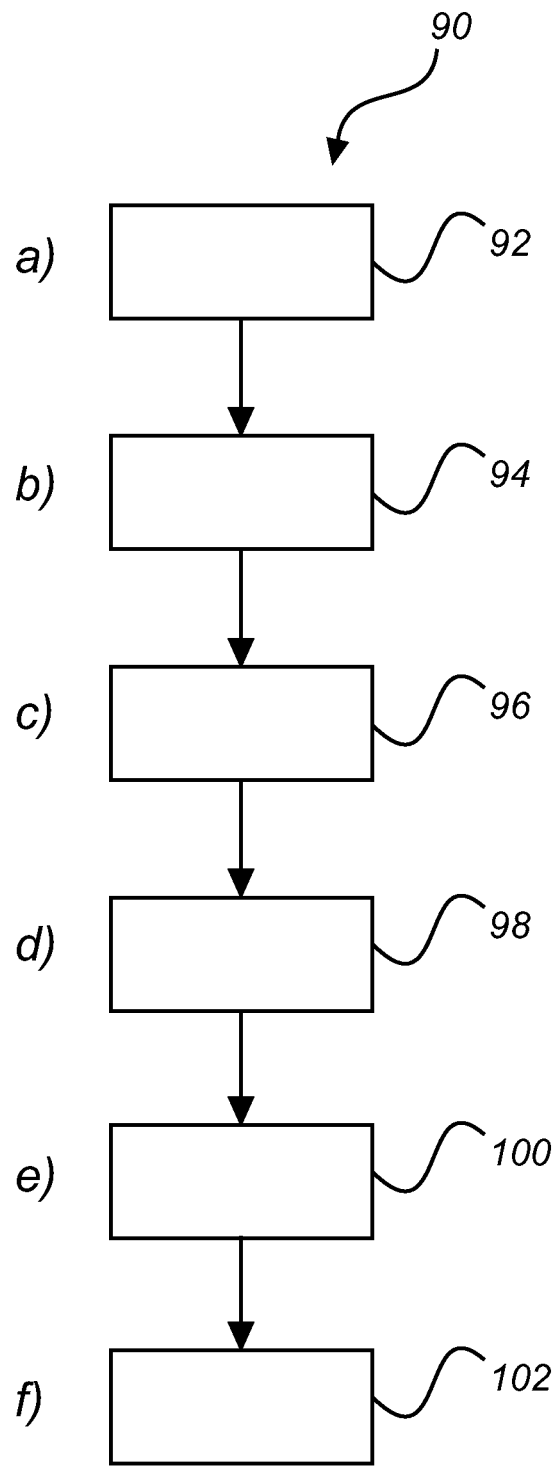
FIG. 6 shows a method according to a third aspect.
Figure 7:
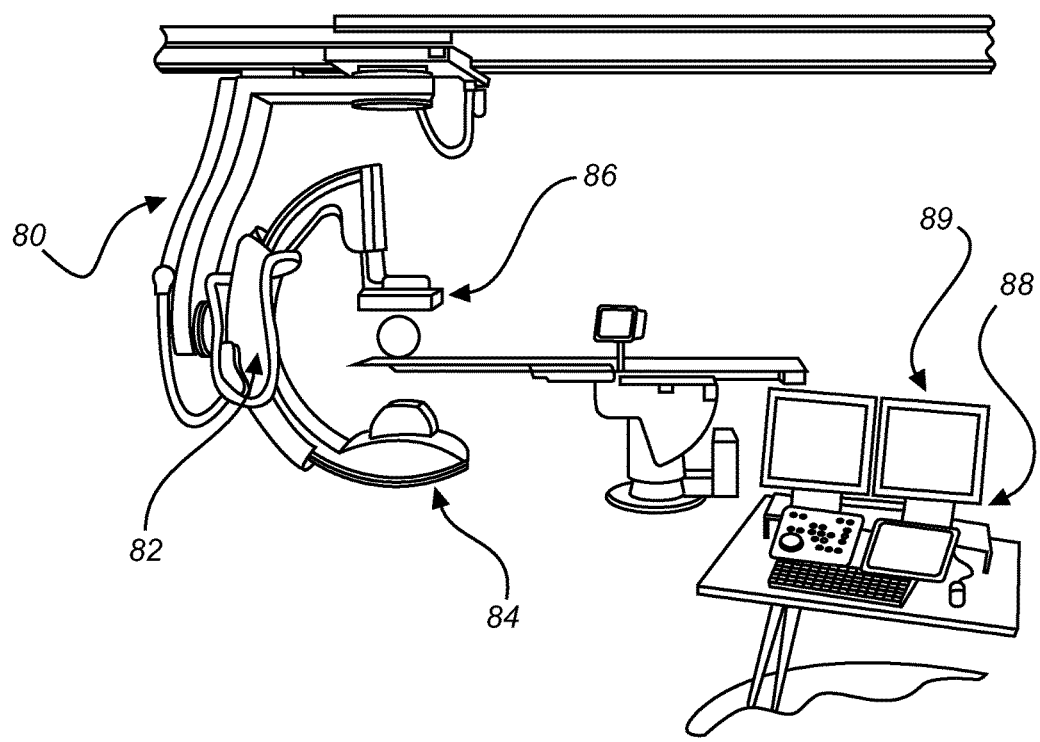
FIG. 7 shows an X-ray system according to a second aspect.

According to an embodiment of the invention, the detection box 46 is additionally configured to perform device identification. There are, thus, configuration reference maps for different types of intervention devices. A configuration reference map corresponding to the identified intervention device is selected, as shown in box 48. The configuration reference map contains specific deformation data for the reference intervention device information 41. The specific deformation data provides deformation bounds which are specific to the associated intervention device. In other words, a replacement heart valve stent in an un-deployed state may deform in a different way than an injection catheter, for example. Provision of specific deformation data enables this fact to be exploited in a registration. In the first registration 50, the specific deformation data for the identified specific intervention device is used to improve the accuracy of the first registration. FIG. 5 shows another representation of the described technique is shown. FIG. 5*a*) shows a typical record 60 of a configuration reference map. The record comprises reference object information 62 (a generic vasculature) and reference intervention device information 64 (a generic deployment of an intervention device inside the generic vasculature). The reference object information 62 is shown in the form of an arcuate vessel boundary. The reference intervention device information 64 is shown as an intervention device. The intervention device is shown in dashes against the outer border of the vessel.

FIG. 5*b*) shows a fluoroscopic image 66 with an intervention device 68 (a stent) in an aortic arch. Therefore, FIG. 5*b*) shows a representation of intervention image data. Notably, the form of the intervention device 68 in the live intervention image data is similar to that of the reference object information 62 in FIG. 5*a*).

FIG. 5*c*) shows a 3D segmentation of a patient aorta in a pre-operative CT data set 70. Thus, FIG. 5*c*) shows an example of object data. Notably, the 3D segmentation comprises a section having a curve comparable in shape to the reference object information 62.

FIG. 5*d*) shows aspects of a registration of the live intervention image data and the object data without using the data in the configuration reference map. Contours of the object data are represented as an outline 72. As can be seen, the outline 72 of the object data is not well aligned with the intervention device 74 or even the general anatomy of the patient in the live intervention image.

FIG. 5*e*) shows a device-based registration produced using the configuration reference map. As can be seen, the boundary of the contour 76, representing a contour of the object data, is well aligned with the intervention device 78, and the anatomy of the patient.

Therefore, an effective method of intervention image registration with object data has been provided which exploits a prior configuration reference map comprising reference object information and reference intervention device information.

According to an embodiment of the invention, an apparatus is provided as described above, wherein the processing unit 34 is further configured to detect intervention device data, representing an intervention device, in the intervention image data of the region of interest.

According to an embodiment of the invention, an apparatus is provided according to the previous description, wherein the processing unit 34 is further configured to provide a plurality of configuration reference maps, wherein each configuration reference map of the plurality of configuration reference maps provides different combinations of (i) reference object information and (ii) reference intervention device information.

According to this embodiment, a wide range of candidate vasculatures and candidate reference intervention devices may be provided in a database to enable more accurate and flexible registration using different patient anatomies and different intervention devices.

According to an embodiment of the invention, an apparatus is provided, wherein the processor 34 is configured to select the matched configuration reference map registration as a reference map which optimizes a similarity match metric between the plurality of configuration reference maps and the intervention device information.

According to this embodiment, a wide range of intervention devices may be represented in the configuration reference maps. The reference intervention device information which is closest in a shape to the intervention device information may be selected, based on a similarity match metric. Such a similarity match metric may be computed based on a least square estimation, or another estimation technique.

According to an embodiment of the invention, an apparatus as previously described is provided. The reference object information and/or the reference intervention device information of the configuration reference maps includes parameterizable elements.

The processor 34 is further configured to calculate parameters of the parameterizable elements by comparing the intervention device information to the reference intervention device information, and/or by comparing the object data with the reference object information of the matched configuration reference map registration. The processor is configured to adjust the shape of the parameterizable elements of the reference object information of the configuration reference maps using the calculated parameters.

Intervention devices may have many different sizes (for different patient sizes, for example), even though they have a similar shape. Therefore, this embodiment of the invention enables the detection of intervention devices having a similar shape, by varying the size parameter of the reference intervention device.

According to an embodiment of the invention, the first and/or second registrations are deformable registrations.

According to an embodiment of the invention, an apparatus is provided as previously described, wherein the device further comprises an output device. The output device is further configured to display the adapted image road map comprising the final image.

According to an embodiment of the invention, an apparatus is provided as previously described, wherein the input unit is further configured to provide and/or to update the configuration reference maps by a download from an internet server or related transfer medium.

According to an embodiment of the invention, the object data of a region of interest of an object is provided as 3D image data. The intervention image data is provided as 2D image data from a kinematic X-ray imaging system such as a fluoroscope (live data), and the configuration reference map is provided as a 2D image. Thus, according to this embodiment, the first registration is a 2D to 2D registration, and the second registration is a 3D to 2D registration.

According to an embodiment of the invention, the object data of a region of interest of an object is provided as 3D image data. The intervention image data is provided as 2D image data from a kinematic X-ray imaging system such as a fluoroscope (live data), and the configuration reference map is provided as a 3D image. Thus, according to this embodiment, the first registration is a 2D to 3D registration, and the second registration is a 3D to 3D registration.

According to an embodiment of the invention, the object data of a region of interest of an object is provided as 2D image data. The intervention image data is provided as 2D image data from a kinematic X-ray imaging system such as a fluoroscope (live data), and the configuration reference map is provided as a 2D image. Thus, according to this embodiment, the first registration is a 2D to 2D registration, and the second registration is a 2D to 2D registration.

According to an embodiment of the invention, the object data of a region of interest of an object is provided as 3D image data. The intervention image data is provided as 3D image data (live data), and the configuration reference map is provided as a 3D image. Thus, according to this embodiment, the first registration is a 3D to 3D registration, and the second registration is a 3D to 3D registration.

According to an embodiment of the invention, the object data of a region of interest of an object is provided as 3D image data. The intervention image data is provided as 2D image data from a kinematic X-ray imaging system such as a fluoroscope, and the processing unit is configured to provide the first registration as a 2D/3D registration, and to provide the second registration as a 3D/3D registration.

According to an embodiment of the invention, the object data of a region of interest of an object is provided as 2D image data. The intervention image data is provided as 2D image data from a kinematic X-ray imaging system such as a fluoroscope, and the processing unit is configured to provide the first registration as a 2D/2D registration, and to provide the second registration as a 2D/2D registration.

According to an embodiment of the invention, the input unit 32 is additionally configured to receive intervention image alignment data (acquisition geometry), comprising a polar angle and an azimuth angle of the intervention imager (fluoroscope) as it images a patient. The intervention image alignment data is used to initialize and constrain the second registration. According to an embodiment of the invention, the configuration reference map additionally comprises (iv) deployment state information of for some items of reference intervention device information. The processor is configured to identify, in the live intervention image data, a deployment state or partial deployment state of the intervention device. The processor is configured to match the identified deployment state or partial deployment state with the deployment state information of the configuration reference map when searching for the matched configuration reference map.

Thus, an expandable device is a parameterizable element, and a deployment state parameter can thus be estimated during the process.

According to the previously discussed embodiment, the configuration reference map includes deployment state information. Therefore, when a stent is identified in live data, the deployment state may also be used to improve the accuracy of a configuration reference map match.

According to an embodiment of the invention, the matched configuration reference map registration is selected from a limited set of configuration reference maps comprising reference intervention device information of a detected reference intervention device, wherein each member of the limited set has different deployment state information.

According to an embodiment of the invention, the intervention device information comprises a sequence having a plurality of image frames. The processing unit 34 is configured to apply the first registration and the second registration successively to each frame of the sequence of frames. Therefore, the accuracy of the first and second registrations can be improved even as the shape of the intervention device in the live intervention image data changes.

According to an example, temporal regularization between frames can be applied to the registration process, and/or the selection of configuration reference map.

According to a second aspect of the invention, there is provided an X-ray imaging system 80.

The X-ray imaging system 80 comprises an X-ray acquisition device 82 with an X-ray source 84 and an X-ray detector 86 for capturing live X-ray images. The X-ray imaging system 80 also comprises an apparatus 88 for intervention device based registration in adaptive image road mapping of an object of interest as previously described. The X-ray imaging system 80 also comprises a display device 89.

The X-ray imaging system 80 is configured to acquire live X-ray image data of a region of interest of an object, to provide the live X-ray image data to the input device of the apparatus 88 for adaptive image road mapping, and to display the live X-ray images with an adaptive image roadmap on the display device 89.

According to the third aspect of the invention, there is provided a method 90 for adaptive image road mapping of an object of interest. The method comprises the steps of:
a) providing 92 object data of a region of interest of an object;
b) providing 94 intervention image data of the region of interest, wherein the image comprises intervention device information of an intervention device positioned in the region of interest;
c) providing 96 a configuration reference map, wherein the configuration reference map comprises (i) reference object information and (ii) reference intervention device information of a reference intervention device inside the reference object information;
d) performing 98 a first registration to match the intervention device information to the reference intervention device information in the configuration reference map, to yield a matched configuration reference map registration;
e) performing 100 a second registration to match the object data with the reference object information of the matched configuration reference map to yield the object data registration; and
f) combining 102 the matched configuration reference map registration and the object data registration to yield final roadmap image data.

According to the previous method, there is provided an embodiment as previously described, wherein in step d), the matched configuration reference map registration is selected as the reference map which optimizes a similarity match metric between the plurality of configuration reference maps and the intervention device information.

According to an embodiment of the invention, a method is provided according to the previous description, in which in step c), a plurality of configuration reference maps is provided, wherein each configuration reference map of the plurality of configuration reference maps provides different combinations of (i) reference object information and (ii) reference intervention device information.

According to an embodiment of the invention, a method is provided according to the previous description, in which in step c), the reference object information and/or the reference intervention device information of the configuration reference maps includes parameterizable elements. In a subsequent step c1), parameters of the parameterizable elements are calculated by comparing the intervention device information to the reference intervention device information, and/or by comparing the object data with the reference object information of the matched configuration reference map registration. In a subsequent step c2), the shape of the parameterizable elements of the reference object information of the configuration reference maps is adjusted, using the calculated parameters.

According to an embodiment of the invention, a method is provided according to the previous description, in which in step d) and/or e), the first and/or second registrations are deformable registrations.

According to an embodiment of the invention, a method is provided according to the previous description, comprising the further step g) of displaying the adapted image roadmap comprising the final roadmap image data.

According to an embodiment of the invention, a method is provided according to the previous description wherein in step c), there is the step c3) of providing and/or updating the configuration reference maps by a download from an internet server or a data transfer medium.

According to an embodiment of the invention, a method is provided according to the previous description, wherein in step c), the object data of a region of interest of an object is provided as 3D image data. Furthermore, in step b), the intervention image data is provided as 2D image data from a kinematic X-ray imaging device. Furthermore, in step e), the first registration is provided as a 2D/3D registration, and in step f), the second registration is provided as a 3D/3D registration.

According to an aspect of the invention, a computer program element for controlling an apparatus according to one of the previous description is provided, wherein the computer program element is executed by a processing unit, to perform the method steps according to any of the previously described method steps.

According to an aspect of the invention, a computer-readable medium is provided, having stored the program element as previously described.

According to an aspect of the invention, there is provided a computer-readable medium having stored the program element described previously.

A computer program element might therefore be stored on a computer unit, which might also be an embodiment of the present invention. This computing unit may be adapted to perform or induce performance of the steps of the method described above. Moreover, it may be adapted to operate the components of the above-described apparatus. The computing unit can be adapted to operate automatically and/or to execute orders of a user. A computer program may be loaded into a working memory of a data processor. The data processor may thus be equipped to carry out the method of the invention.

This exemplary embodiment of the invention covers both the computer program that has the intervention installed from the beginning, and a computer program that by means of an update turns an existing program into a program that uses the invention.

A computer program may be stored and/or distributed on a suitable medium, such as an optical storage media, or a solid state medium supplied together with, or as a part of other hardware, but may also be distributed in other forms, such as via the Internet or other wired or wireless telecommunication systems. However, the computer program may also be presented over a network like the World Wide Web, and can also be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It should be noted that embodiments of the invention are described with reference to different subject-matters. In particular, some embodiments are described with reference to method-type claims, whereas other embodiments are described with reference to device-type claims. However, a person skilled in the art will gather from the above, and the following description that, unless otherwise notified, in addition to any combination of features belonging to one type of subject-matter, also other combinations between features relating to different subject-matters is considered to be disclosed with this application.

All features can be combined to provide a synergetic effect that is more than the simple summation of the features.

While the invention has been illustrated and described in detail in the drawings and foregoing description, such illustration and description are to be considered illustrative or exemplary, and not restrictive. The invention is not limited to the disclosed embodiments.

Other variations to the disclosed embodiments can be understood, and effected by those skilled in the art in practicing the claimed invention, from a study of the drawings, the disclosure, and the dependent claims.

In the claims, the word "comprising" does not exclude other elements or steps, and the indefinite article "a" or "an" does not exclude a plurality. A single processor, or other unit, may fulfil the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. An X-ray imaging system for adaptive image roadmapping of an object during an intervention procedure, the imaging system comprising:
    an X-ray acquisition device comprising an X-ray source and an X-ray detector for capturing live X-ray images of a region of interest of the object;
    a processor programmed to:
        receive previously acquired object data of the region of interest of the object;
        receive intervention image data from a live intervention image of the region of interest from the X-ray acquisition device during the intervention procedure, wherein the intervention image data comprises intervention device information of an intervention device positioned in the region of interest;
        receive a configuration reference map from a configuration reference map database, wherein the configuration reference map comprises: (i) reference object information of a reference object and (ii) reference intervention device information of a reference intervention device inside the reference object;
        perform a first registration to match the intervention device information to the reference intervention device information in the configuration reference map to yield a matched configuration reference map registration;
        perform a second registration to match the object data with the reference object information of the matched configuration reference map to yield an object data registration; and
        combine the matched configuration reference map registration and the object data registration to yield final roadmap image data; and
    a display device configured to display the live intervention image with the final roadmap image data.

2. The imaging system of claim 1,
wherein the processor is further programmed to select the matched configuration reference map from a plurality of configuration reference maps, wherein each configuration reference map of the plurality of configuration reference maps provides different combinations of (i) reference object information and (ii) reference intervention device information.

3. The imaging system of claim 2,
wherein the processor is further programmed to select the matched configuration reference map by optimizing a similarity match metric between the plurality of configuration reference maps and the intervention device information.

4. The imaging system of claim 2,
wherein at least one of the reference object information or the reference intervention device information of the configuration reference maps includes parameterizable elements; and wherein the processor is further programmed to calculate parameters of the parameterizable elements by at least one of comparing the intervention object information to the reference device information, or comparing the object data with the reference object information of the matched configuration reference map; and to adjust a shape of the parameterizable elements of the reference object information of the configuration reference maps using the calculated parameters.

5. The imaging system of claim 1,
wherein at least one of the first or second registrations is deformable registrations.

6. The imaging system of claim 1,
wherein the processor is further programmed to update the configuration reference map by a download from an internet server.

7. The imaging system of claim 6,
wherein the object data of the region of interest of the object is provided as 3D image data; wherein the intervention image data is provided as 2D image data; and wherein the processor is further programmed to provide the first registration as a 2D/3D registration, and to provide the second registration as a 3D/3D registration.

8. The imaging system of claim 1,
wherein the processor is further programmed to update the configuration reference map by a download from a data transfer medium.

9. The imaging system of claim 1,
wherein the previously acquired object data is from at least one CT image of the region of interest of the object acquired before the intervention procedure, and wherein the live intervention image is a fluoroscopic image acquired during the intervention procedure.

10. A method for adaptive image roadmapping of an object by an X-ray imaging apparatus during an intervention procedure, the method comprising:
receiving, by the X-ray imaging apparatus, object data previously acquired of a region of interest of the object;
receiving, by the X-ray imaging apparatus, intervention image data from a live intervention image of the region of interest from an X-ray acquisition device acquiring live X-ray images of the region of interest, during the intervention procedure, wherein the intervention image data comprises intervention device information of an intervention device positioned in the region of interest for the intervention procedure;
providing, by a configuration reference map database, a configuration reference map, wherein the configuration reference map comprises: (i) reference object information of a reference object and (ii) reference intervention device information of a reference intervention device inside the reference object;
performing, by the X-ray imaging apparatus, a first registration to match the intervention device information from the intervention image data to the reference intervention device information in the configuration reference map, to yield a matched configuration reference map registration;
performing, by the X-ray imaging apparatus, a second registration to match the object data with the reference object information of the matched configuration reference map to yield an object data registration;
combining, by the X-ray imaging apparatus, the matched configuration reference map registration and the object data registration to yield final roadmap image data; and
displaying, by a display device, at least the final roadmap image data during the intervention procedure.

11. The method of claim 10, further comprising:
selecting the matched configuration reference map from a plurality of configuration reference maps, wherein each configuration reference map of the plurality of configuration reference maps provides different combinations of (i) reference object information and (ii) reference intervention device information.

12. The method of claim 11,
wherein selecting the matched configuration reference map comprises optimizing a similarity match metric between the plurality of configuration reference maps and the intervention device information.

13. The method of claim 10,
wherein the previously acquired object data is from at least one CT image of the region of interest of the object acquired before the intervention procedure, and wherein the live intervention image is a fluoroscopic image acquired during the intervention procedure.

14. The method of claim 10,
wherein the object data is 3D image data, and the intervention image data is 2D image data, and wherein performing the first registration comprises a 2D/3D registration, and performing the second registration comprises a 3D/3D registration.

15. A non-transitory computer readable medium that stores a computer program with instructions for performing adaptive image roadmapping of an object by an X-ray imaging apparatus during an endovascular procedure, the instructions, when executed by a processor of an X-ray imaging apparatus, cause the processor to:
receive object data previously acquired of a region of interest of the object;
receive intervention image data from a live intervention image of the region of interest, from an X-ray acquisition device acquiring live X-ray images of the region of interest, during the endovascular procedure, wherein the intervention image data comprises intervention device information of an intervention device positioned in the region of interest for performing the intervention procedure;
receive a configuration reference map from a configuration reference map database, wherein the configuration reference map comprises: (i) reference object information of a reference object and (ii) reference intervention device information of a reference intervention device inside the reference object;
perform a first registration to match the intervention device information from the intervention image data to the reference intervention device information in the configuration reference map to yield a matched configuration reference map registration;
perform a second registration to match the object data with the reference object information of the matched configuration reference map to yield an object data registration;
combine the matched configuration reference map registration and the object data registration to yield final roadmap image data; and
cause the final roadmap image data to be displayed, by a display device, during the endovascular procedure.

16. The non-transitory computer readable medium of claim 15, wherein the instruction further cause the processor to:
select the matched configuration reference map from a plurality of configuration reference maps, wherein each configuration reference map of the plurality of configuration reference maps provides different combinations of (i) reference object information and (ii) reference intervention device information.

17. The non-transitory computer readable medium of claim 16,
wherein the matched configuration reference map is selected by optimizing a similarity match metric between the plurality of configuration reference maps and the intervention device information.

18. The non-transitory computer readable medium of claim 15,
wherein the previously acquired object data is from at least one CT image of the region of interest of the object acquired before the endovascular procedure, and wherein the live intervention image is a fluoroscopic image acquired during the endovascular procedure.

19. The non-transitory computer readable medium of claim 15,
wherein the object data is 3D image data, and the intervention image data is 2D image data, and wherein the first registration is performed as a 2D/3D registration, and the second registration is performed as a 3D/3D registration.

\* \* \* \* \*